(12) United States Patent
Schwartz

(10) Patent No.: US 8,034,550 B2
(45) Date of Patent: Oct. 11, 2011

(54) CHEMICAL SCREENING SYSTEM USING STRIP ARRAYS

(75) Inventor: David C. Schwartz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 620 days.

(21) Appl. No.: 12/128,928

(22) Filed: May 29, 2008

(65) Prior Publication Data

US 2009/0054265 A1    Feb. 26, 2009

Related U.S. Application Data

(62) Division of application No. 09/638,102, filed on Aug. 11, 2000, now abandoned.

(51) Int. Cl.
*C12Q 1/00* (2006.01)
(52) U.S. Cl. .......................................... 435/4
(58) Field of Classification Search .................. None
See application file for complete search history.

(56) References Cited

U.S. PATENT DOCUMENTS

| | | | | |
|---|---|---|---|---|
| 6,136,549 | A | * | 10/2000 | Feistel .......................... 435/7.1 |
| 6,660,233 | B1 | * | 12/2003 | Coassin et al. ................ 422/564 |
| 7,473,547 | B2 | * | 1/2009 | Ogura ........................ 435/287.1 |

* cited by examiner

*Primary Examiner* — Ann Lam
(74) *Attorney, Agent, or Firm* — Boyle Fredrickson, S.C.

(57) ABSTRACT

Arrays of distinct chemically reactive materials used for assaying or screening are assembled by arranging premanufactured strips, each having a linear array of chemically reactive materials on its surface, into a frame to be exposed to a substance to be analyzed. The strips provide great flexibility in generating different types of arrays while still permitting efficiencies to be gained by batch processing of each strip type. The arrays further provide for novel read-out and reaction promotion techniques making use of the ability of the strips to direct and received energy to and from particular sites.

16 Claims, 6 Drawing Sheets

CHEMICAL SCREENING SYSTEM USING STRIP ARRAYS

CROSS-REFERENCE TO RELATED APPLICATIONS

This application is a divisional of U.S. patent application Ser. No. 09/638,102, filed Aug. 11, 2000, now abandoned and hereby incorporated by reference in its entirety.

STATEMENT REGARDING FEDERALLY SPONSORED RESEARCH OR DEVELOPMENT

This invention was made with U.S. government support by the following agency: NIH Grant No. HG00225. The United States government has certain rights in this invention.

BACKGROUND OF THE INVENTION

The present invention relates to devices for screening attributes of chemical compounds, and in particular, to a method and apparatus for flexibly producing arrays of different chemically active substances for large scale chemical screening and assaying.

The analysis of chemical substances (e.g., nucleotide sequences) may be facilitated by the preparation of an array having many different chemical compounds (sampling compounds) placed at known sites. Each sampling compound selectively bonds with a different substance that may be part of the material to be analyzed. The sampling compounds are arranged in a regular pattern of array elements over the plane of the array.

In the field of genetic research, the sampling compounds may be different oligonucleotides at least one of which is expected to hybridize with portions of a genetic material to be tested. Fluorescent or radioactive markers bonded to the genetic material to be tested, or other well-known techniques, may be used to determine the location of the hybridizations, and from these locations (and a map of known locations of the sample oligonucleotides in the planar array), information about the make-up or other attributes of the genetic material may be determined.

A number of different methods have been used to create such arrays of different sampling compounds. In one sequential method, different sampling compounds are synthesized and placed in different wells of a microtiter place. The sampling compounds are then transferred from a microtiter plate to one or more array substrates by a robotically controlled dipping stick immersed first in a sampling compound then touched to different elements of the array where that sampling compound is to be located. In the case where the sampling compounds are oligonucleotides, the components are nucleic acids generated by using PCR and suitable templates.

A variation on this system, particularly useful in the generation of oligonucleotides, employs an ink jet-type process similar to that used in standard commercial printers to build up the sampling compounds, one component at a time, through layers laid down on particular elements of the array in a spatially controlled manner. For oligonucleotides, the process cycles through each of the four nucleic acids so that arbitrary oligonucleotides may be formed at the different array elements.

An alternative approach that processes many elements in parallel creates a series of masks, for example, using photolithographic techniques, where the masks have openings over specified array elements where a component is to be deposited. After each mask is in place, the desired component is washed over the mask and attaches only to those array elements corresponding to an open mask position. The mask is then removed and a new mask laid in place and this process repeated with a different component, for example, a different nucleic acid.

The laborious process of generating, applying and removing masks may be eliminated through the use photo-activation techniques in which the constituent components to be applied to array elements are suffused at the surface of the array and selective array elements irradiated with light to bond the components only at the illuminated elements. Mirror systems using micro-machined mirrors to direct intense light selectively to different portions in the array provide simultaneous processing of many array elements.

While this last technique eliminates the need for mask generation, constraints in maximum light flux that can be controlled, limit the speed at which arrays may be formed. Generally, mask techniques will be used when large numbers of a given type of array must be produced and sequential or mask-less photo activation techniques will be used for limited productions of different types of arrays.

A tradeoff between the speed of manufacturing the arrays and flexibility in manufacturing arrays of different types is provided by forming the different sampling compounds of an array on small beads. Those beads having a given sampling compound may be manufactured using parallel processing techniques. Later, beads with different sampling compounds are mechanically assembled into arrays using robotic manipulation or the like.

It is in this latter stage of manipulating the beads into usable arrays, that the shortcoming of using beads becomes most pronounced, and that causes, as a practical matter, the use of beads in manufacturing planar arrays, to be limited.

BRIEF SUMMARY OF THE INVENTION

Rather than placing sampling compounds on beads or in planar arrays, the present invention places the sampling compounds in linear arrays on slender strips. Multiple strips may be processed in parallel to obtain the benefit of efficient production of large numbers of the strips. Yet, the strips are easily handled and identified and may be assembled into dense, planar arrays with desired, arbitrary row variations. By using strips, an improved tradeoff between mass production and flexibility is obtained.

The strips further enable a variety of novel techniques of detecting and promoting the reactions of interest. In these techniques, the strips provide conduits for light or electrical energy.

Specifically then, the present invention provides a chemical screening apparatus having at least two different strips of a non-reactive substrate extending along a longitudinal axis and, supporting spaced along that longitudinal axis, a linear array of different chemically reactive sampling compounds exposed on a surface of the strip. A support frame receives and holds the strips for mutual exposure to a material to be screened.

Thus it is one object of the invention to facilitate the screening of a chemical compound against large numbers of sampling compounds in an efficient and yet flexible way. Each strip may be manufactured in a batch including many other strips and, then separated from the batch and assembled to produce a variety of different arrays.

The support frame may hold the strips transversely spaced in parallel relationship.

Thus it is another object of the invention to provide for a high density planar array of sampling compounds using easily manufactured strips.

The support frame may also hold strips transversely spaced along two 30 perpendicular axes.

Thus it is another object of the invention to enable the creation of three-dimensional arrays of sampling compounds allowing efficient sampling for many thousands of materials.

The strips may include isolating bands of repellant coatings between the sampling compounds or recessed portions receiving the sampling compounds.

Thus it is another object of the invention to facilitate the precise location of the sampling compounds, less cross contamination between the sampling compounds and greater densities of the sampling compounds on the strip.

The strip may include a marker allowing the strip to be uniquely identified, for example, using printing or fluorescent material and allowing a given end of the strip to be identified.

Thus it is another object of the invention to overcome a significant problem with beads being the difficulty of labeling the beads. An ample portion of the strip is available for marking without adversely affecting the density of sampling compounds and such marking may therefore use relatively simple techniques such as bar coding or the like.

The present invention allows for a number of methods of manufacturing the strips. In one method, the strips are fixed in a frame to be transversely spaced in parallel relationship in a plane to expose at a plane surface locations for the sampling compounds. The frame is then immersed in a sequence of component solutions. The solutions may be light activated to bond their components to the strips at a subset of locations for each of a set of different components or may be controlled through the use of masks to similar effect. After the series of component solutions has been applied, the frame may be removed and the strips released from the frame.

Thus it is one object of the invention to apply the same techniques now applied to the manufacture of planar arrays of sampling compounds to the manufacture of strips. Flexibility in the assembly of the arrays is preserved by the later release of the strips from the frame.

In a second method of manufacture, a strip is positioned having different longitudinal portions in adjacent volumes holding different component solutions. Light then activates a bonding of the components of the solutions with the strip at locations for at least one of the sampling compounds. The strip is then repositioned within the volumes of different component solutions and these steps are repeated to create the sampling compounds at the locations.

Thus it is another object of the invention to make use of the linear nature of the strips to allow for rapid fabrication on semi-continuous basis of the chemically reactive compounds. The strips may be easily moved between baths of a component solution in a way that would not be possible with planar arrays.

In yet another method of manufacture, the strips may be positioned to pass through a volume bracketing a segment of the strips. Once positioned, the volume may be filled with the component solution bonding a substance of that solution onto the segment to form a portion of the sampling compounds. The volume may be then flushed of component solution and the strip repositioned. These steps may be repeated with different component solutions to create the sampling compounds at the locations.

Thus it is another object of the invention to provide for rapid manufacture of the strips without the need for light activating techniques. In this case, the volumes serve as atomistic masks that need no changing as arbitrary sequences sampling compounds are deposited.

The present invention may also be used for manufacture of beads. In such manufacture, strips are prepared and then are cut between the locations where the sampling compounds are found.

It is thus another object of the invention to eliminate much of the handling problems of the creation of such beads.

The present invention also provides a method of automatic read-out of reactions between the sampling compounds and an analyzed material. In this method, two different strips are prepared and arranged to cross at a read-out site. Energy is emitted from an energetic interaction with a sampling compound at the read-out site. Energy from the read-out side is detected as conducted by at least one of the strips.

Thus it is another object of the invention to make use of the energy carrying and isolating capacity of strip substrates to simplify the read-out process.

In a similar way, the strip substrates may be used to promote reactions at particular sites. In this case, at least two strips are arranged to cross at a promotion site. Energy is applied to at least one of the strips to promote an energetic interaction with a sampling compound at the promotion site causing a localized chemical reaction.

Thus it is another object of the invention to provide for more complex assaying and screening techniques requiring intermediary reactions selectively controlled at specific array elements.

These objects will not be realized by all embodiments of the invention. For this reason, the objects should not be considered as limiting the scope of the invention. The scope of the invention should be determined by reference to the claims. A preferred embodiment is also described. The preferred embodiment is not exhaustive of all practical embodiments of the invention nor is it intended to be. For this reason, again, the claims should be consulted to determine the scope of the invention.

DETAILED DESCRIPTION OF THE INVENTION

Figure 1:
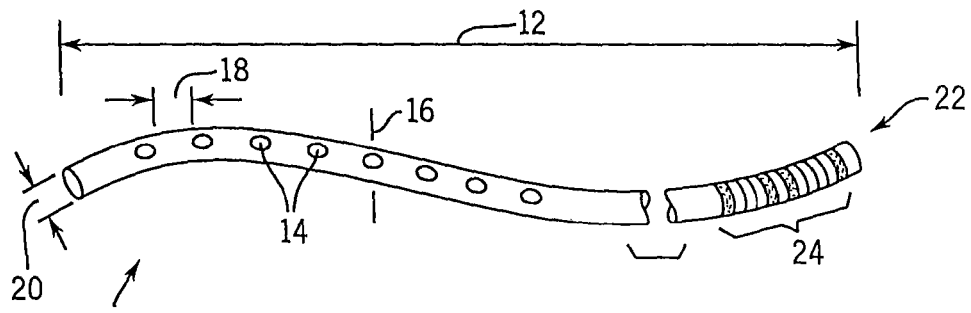
FIG. 1 is an enlarged fragmentary view of a single strip per the present invention showing sampling sites at which sampling compounds are in place and a strip label at one end of the strip.

Referring now to FIG. 1, a filament 10 of the present invention extends along a longitudinal axis by a length 12 to provide, at an exposed outer surface of the filament, a number of different chemically reactive substances henceforth termed sampling compounds 14 spaced at locations 16 by a regular spacing distance 18.

Generally the filament 10 may include a substrate strip of material of low chemical reactivity with the material to be tested and may be constructed of a variety of materials including glass, plastic, carbon and metal. As used herein, the term "strip" is intended to encompass any long, thin member providing substantially a single dimension of locations 16. More precisely, the strip will have a length 12 that will exceed the diameter 20 (or a greatest cross-sectional span for non-round strips) by at least a factor of ten and typically by many thousands of times. The strip may but need not be constructed of a flexible material.

A marker 24 may be placed at one end 22 of the filament 10, so as to allow the filament 10 to be identified and oriented. The marker 24 may be a printed bar code such as may be read automatically by bar code scanners or may be formed by a number of other techniques including characters, fluorescent markings or the like attached directly or indirectly to the end 22.

Figure 2:
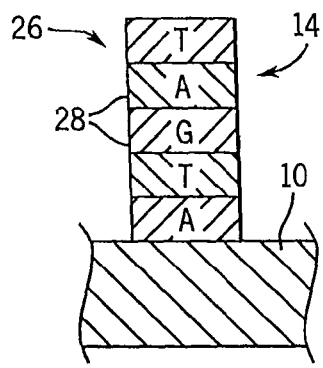
FIG. 2 is an enlarged fragmentary cross section of one sampling site of FIG. 1 showing the assembly of nucleic acids into an oligonucleotide providing a chemically reactive material.

Referring now to FIG. 2, the sampling compounds 14 distributed along the filament 10 in one embodiment are oligonucleotides 26 built up of nucleic acids 28 deposited sequentially onto the preceding nucleic acid as will be described below. Alternatively, but not shown, the sampling compounds may be other chemically reactive compounds synthesized on site at the locations or presynthesized and applied to the locations. Each sampling compound 14 may be unique and their order along the length 12 may be of an arbitrary predetermined sequence. A number of methods of applying the sampling compounds 14 to the filament 10 will be described further below.

Figure 3:
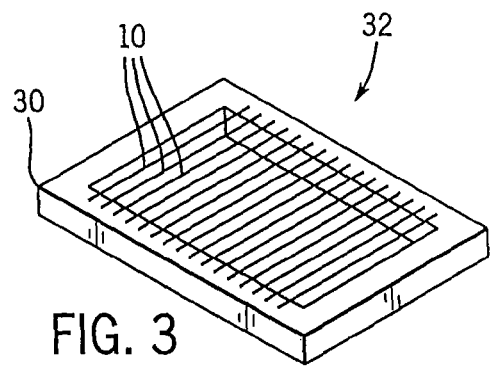
FIG. 3 is a perspective view of a number of strips of FIG. 1 assembled on a frame to achieve high sample density.

Referring now to FIG. 3, the filaments 10 may be used directly for assaying an unknown material. In this regard, a one-meter fiber with ten-micron spacing distance 18 could hold 100,000 sampling compounds 14. Each sampling compound 14 can be identified by its locations and sequence on the filament 10 with respect to the marker 24. When multiple filaments 10 are used, a unique identifier of the marker 24 may distinguish them. Flexibility of the filament 10 can allow it to be coiled within a small volume of tested solutions.

In an alternative embodiment, providing more convenient handling of filaments 10 and providing the ability to vary the sampling compounds 14 while still partaking of possible batch efficiencies in creating the filaments 10, a number of short filaments 10 are attached at their ends on opposite sides of a rectangular frame 30 to span an open area defined thereby. Preferably, the ends of the filaments 10 where they are attached are free from sampling compounds 14 and may be retained by adhesive or mechanical clamps or other well-known techniques. A fifty-micron diameter fiber cut into 200 one-centimeter pieces, could fill a one-by-one centimeter frame 30 with two meters of fibers or about 200,000 sampling compounds 14. In this way an array 32 may be generated.

The use of such arrays 32 is not limited to assaying and screening, terms that will henceforth be used interchangeably, but may also be used for the screening of other materials including generally other organic molecules, peptides and other compounds.

Figure 4:
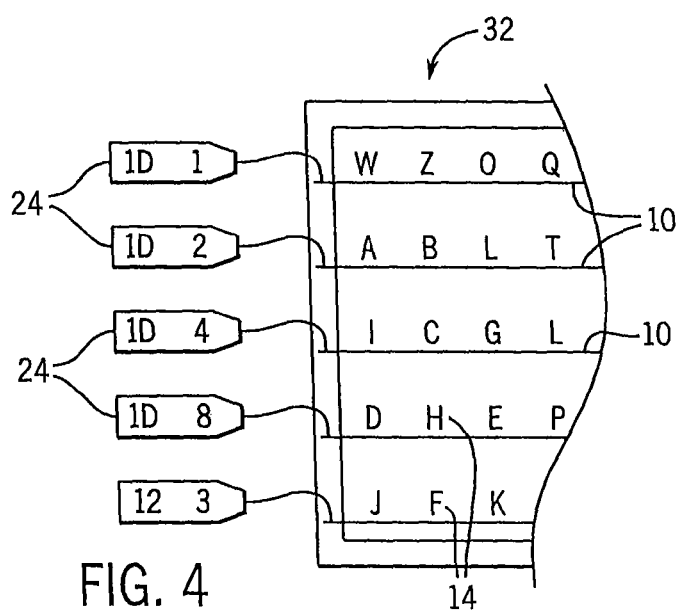
FIG. 4 is a schematic representation of the frame of FIG. 3, showing selection of different strips to generate arbitrary rows of chemically reactive samples as identified by the strip labels.

Referring now to FIG. 4, it will be understood that the technique of assembling short lengths of the filaments 10 into an array 32 allows a wide variety of semi-custom arrays 32 to be created from a more limited set of standard filaments 10. In FIG. 4, the letters indicate different sampling compounds 14. The sequence of sampling compounds 14 of each row formed by a filament 10 will be defined by the set of standard filaments 10. Nevertheless, the number of different arrays 32 will be equal to the mathematical combination of the number of different filament types, a far larger number. For example, from a library of 400 standard fibers, $10^{119}$ different 200 fiber arrays 32 may be created.

In this way, the use of filaments 10 to create an array 32, leverages a limited number of filament types into an extremely flexible variety of arrays 32. The arrays 32 may be assembled efficiently by robotic techniques or the like and may be verified by reading the identification markers 24 unique to each filament.

Figure 5:
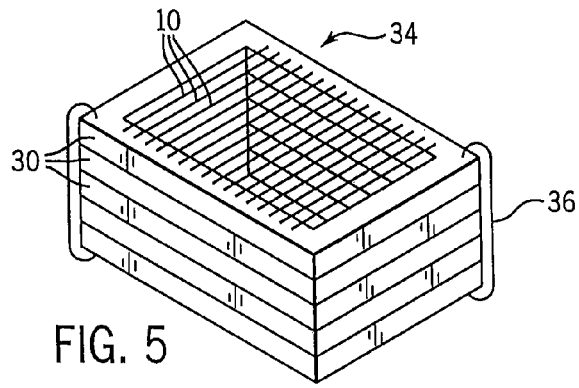
FIG. 5 is a perspective view similar to that of FIG. 3, showing the assembly of a number of frames of FIG. 3 into a volumetric array for high sample densities.

Referring now to FIG. 5, higher volumetric sample densities may be obtained by stacking the frames 30 of FIG. 2 into a column 34 as held by clips 36. In this case, the spaces between the filaments 10, allow ready circulation of material to be analyzed through the frames 30 past the sampling compounds 14 of each of the filaments 10.

Figure 6:
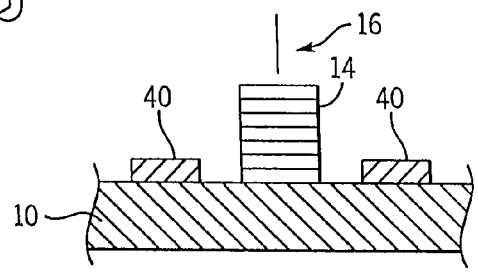
FIG. 6 is a cross-sectional view similar to that of FIG. 2 showing the attachment of guard bands of repellant material to the strips between the sampling sites.

Referring now to FIG. 6, guard bands 40 may be placed on the surface of the filaments 10 between the locations 16 of the sampling compounds 14. These guard bands 40 may be, for example, a repellant such as a siliconized coating or hydrophobic material attached to the filaments 10 prior to placement of the sampling compounds 14 by resist techniques or the like. The guard bands 40 increase the densities of sampling compounds 14 that maybe placed on the filament 10

(reducing the spacing distance 18) while preserving the separation of the sampling compounds 14.

Figure 7:
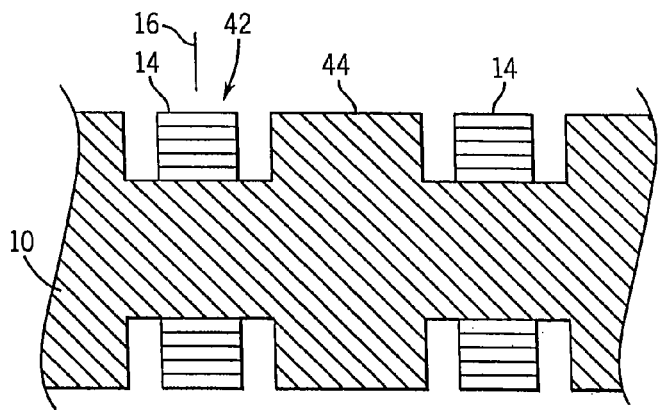
FIG. 7 is a figure similar to that of FIG. 3 showing notching of the strip to receive the chemically reactive material at the sampling sites.

Referring to FIG. 7, the filaments 10 may alternatively or in addition, include notches or pits 42 for receiving the sampling compounds 14 at the locations 16 and thereby providing radially extending walls 44 between sampling compounds 14, offering a function similar to that of the guard bands 40 but also protecting the sampling compounds 14 from mechanical abrasion.

Figure 8:
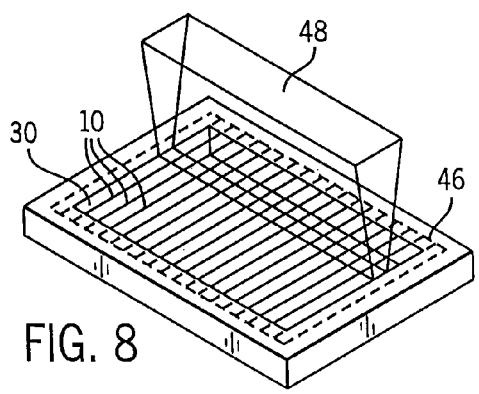
FIG. 8 is a figure showing a frame similar to that of FIG. 3 for batch processing a number of strips using a scanned columnar light source to generate the chemical samples by photo activation techniques.
Figure 9:
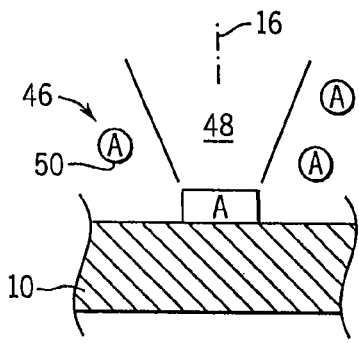
FIG. 9 is a cross-sectional view of one strip of FIG. 8 showing the photo activation of substrate-bound molecules.

Referring now to FIGS. 8 and 9, the ability to offer semi-custom arrays 32 by mixing and matching different filaments 10 is consistent with the filaments 10 being manufactured in batches in which many of the same type of filaments 10 are produced in parallel thus reducing the total manufacture time of a given array 32.

In a first manufacturing technique, strips for use as filaments 10 prior to placement of the sampling compounds 14, may be aligned in a frame 30 similar to that described with respect to FIG. 3 and immersed in a bath 46 holding one of the constituents 50 of the sampling compounds 14. When the sampling compounds 14 are oligonucleotides, the constituents 50 can be individual nucleic acids.

Once the strips of the filaments 10 are in place, a columnar beam of light 48, i.e., a beam of light focused along a column perpendicular to the rows defined by the filaments 10, having a width substantially equal to the width of the sampling compounds 14 as shown in FIG. 1, but substantially less than the spacing distance 18, may illuminate corresponding locations 16 on the strips where it is desired that the constituent 50 be deposited. The light photo activates the constituent materials 50 bound to the surface 46 to further deposit them at the location 16 where the columnar beam of light 48 is located thus attaching them directly to the filament 10 or to another constituent 50 earlier deposited on filament 10. According to techniques similar to those used in the prior art, after the conclusion of the photo activation of a first constituent 50, the frame 30 and filaments 10 are rinsed and immersed in a second bath with a second constituent 50 which may be selectively deposited by photo activation at different locations or the same locations 16. In this way, an arbitrary oligonucleotide may be produced or other similar polymeric chains.

Figure 10:
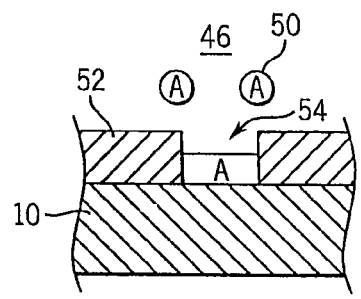
FIG. 10 is a figure similar to that of FIG. 9 showing the localization of the chemically active substance by masks such as may be generated photo lithographically also using columnar light sources similar to those of FIG. 8.

Referring now to FIG. 10, an apparatus holding strips in a frame 30 similar to that shown in FIG. 8 may be used to deposit a photoresist 52 onto the filaments 10 to create a mask covering the filaments 10 except for pockets 54 that allow deposition of the constituent 50 of the bath 46 onto the filament 10 or other earlier constituent 50 deposited at the pocket 54. As is understood in the art, the mask may then be removed by a solvent or other technique and a new mask placed over the filament 10 using a similar photo resist technique. With this new mask in place, a new or the same constituent material 50 may be placed around the filaments 10 in the bath 46 and this process repeated until the necessary polymeric chain is produced.

The mask may be produced photo lithographically through the use of a columnar beam of light 48 similar to that shown in FIG. 9. The filaments 10 are bathed in a photoresist and the light hardens selected columns of a photo resist outside of the pockets 54. Excess photo resist is washed off to produce the necessary mask structure.

In both these cases, a larger number of filaments 10 may be simultaneously processed in the same baths 46 thus significantly improving the efficiency and speed of the manufacturing process on a per array 32 basis.

Figure 11:
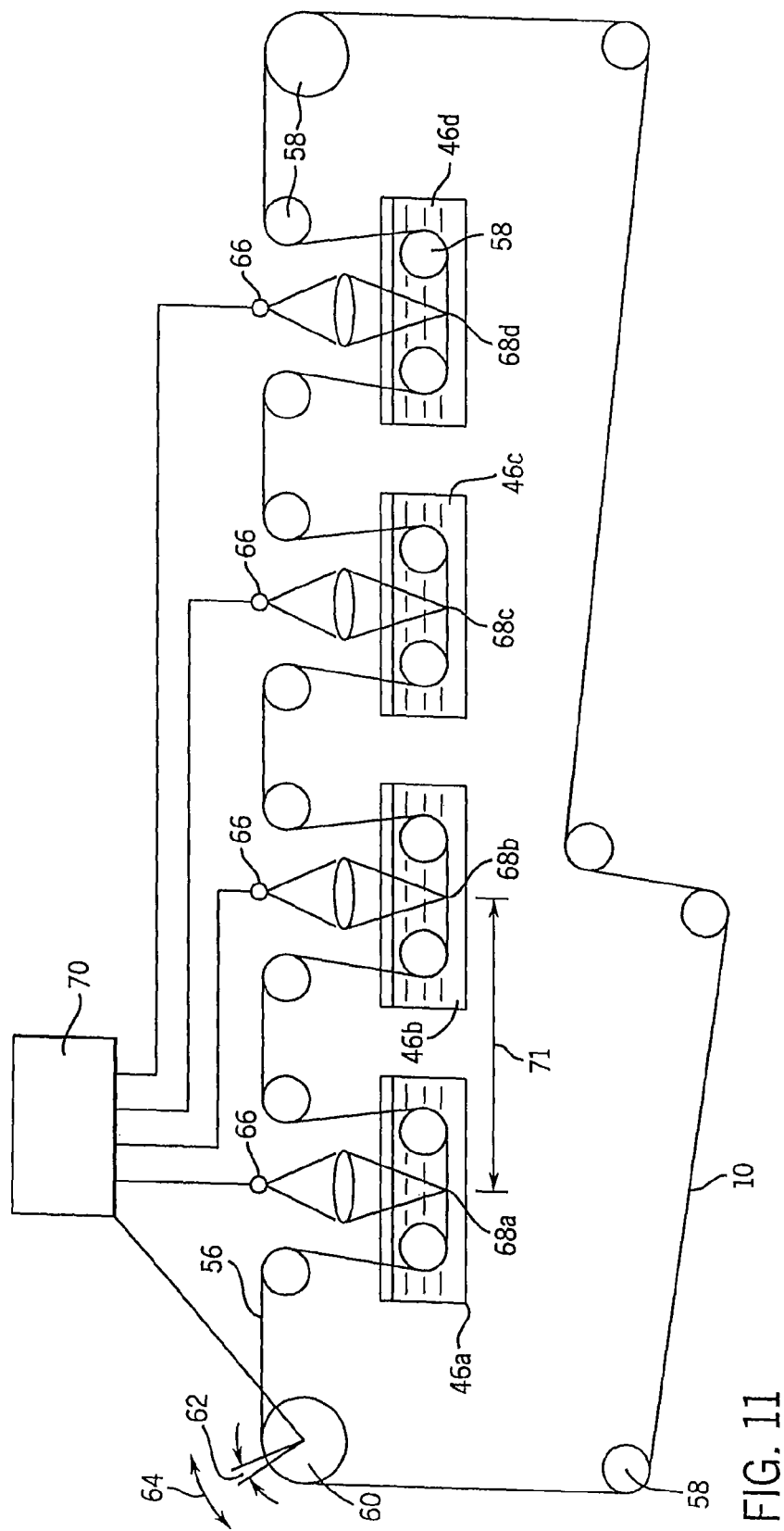
FIG. 11 is a schematic diagram of an assembly line for the manufacture of strips suitable for use with the present invention using a continuous strip circulated through successive baths of chemical components for the chemically active materials.

Referring now to FIG. 11, the structure of the filaments 10 provides for a novel method of manufacturing using a plurality of baths 46a through 46d arranged in a line to receive a strand 56 of the filament 10 passing sequentially through each bath 46a through 46d in sequence. The strand 56 may be continuous as shown, held by a number of idler rollers 58 and advanced by a drive wheel 60, or may be discontinuous and clamped at either end for similar motion as will now be described.

In the former embodiment, the drive wheel 60 moves by an angular increment 62 in either of two directions 64 so as to advance or retreat the filament 10 through the baths 46a through 46d by the spacing distance 18 separating the sampling compounds 14. Rinsing baths, not shown, may be placed between these baths 46a through 46d. Each bath may be associated with an intense light source 66 focused at a corresponding location 68a through 68d on the filament 10 as immersed in a given bath. The separation of the locations 68a through 68d is an integral multiple of the spacing distance 18 between sampling compounds 14.

A computer controller 70, such as a programmable logic controller, coordinates the motion of the wheel 60 and the illumination of selected light sources 66 so as to photo actively deposit the particular constituents 50 of any or all of the baths 46a through 46d on the locations according to a predetermined program. After each illumination step, resulting in the deposition of a constituent material 50 at least one of the baths 46, the computer controller 70 may advance or retreat the filament 10 to a new position and the process repeated until the desired sampling compounds 14 have been built up at the locations 16.

The linear nature of the filament 10 makes this process possible by allowing the filament 10 to be easily moved between baths 46 for rapid generation of the necessary sampling compounds 14s. Because the light sources 66 are fixed, and motion is constrained to motion of the filament 10, the light sources may be easily focused to provide for high light flux commensurate with rapid generation of the necessary compounds. The filament 10 produced by this process may then be broken into a number of separate shorter filaments.

Figure 12:
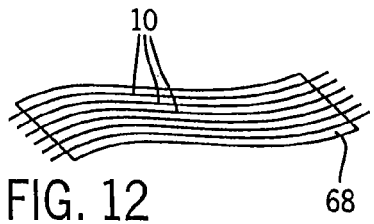
FIG. 12 is a perspective view of a fragment of the strip carrier of FIG. 11 showing a method of processing multiple strips in parallel.

Referring now to FIG. 12, the filament 10 processed as described above with respect to FIG. 11, need not be alone but may be processed in parallel with a number of other filaments 10 on a carrier strip 68. In this case, the light sources 66 are focused into a columnar form similar to that shown in FIG. 8 to cross each of the filaments 10 for parallel processing of those filaments. The filaments 10 may then be removed from the carrier strip 68.

A bar code or other printer (not shown) may be incorporated into the processing line of FIG. 11 to appropriately label the ends and identities of the filaments 10 or of segments from which filaments 10 will be cut. Alternatively, the bar codes or other identifications may be preattached to the filaments prior to the process of FIG. 11.

Figure 13:
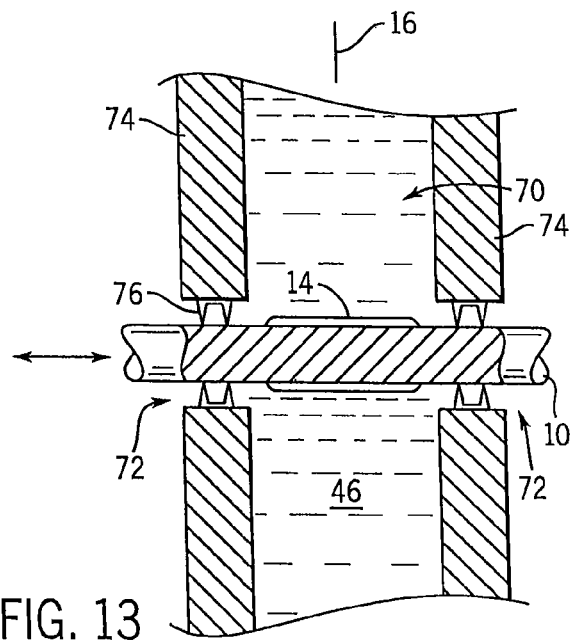
FIG. 13 is cross-sectional view of an alternative method for depositing chemical components on the strip using narrow volume chambers which may be alternately filled and flushed of component material.

Referring now to FIG. 13, using a different manufacturing technique, filaments 10 may be moved through orifices 72 formed in the parallel opposing walls of the volume 71. The orifices may have flexible seals 76 so that the volume may retain a bath 46 of a constituent material to be deposited on the filament 10 while allowing free movement of the filament through the volume 71. The separation of the walls 74 may be commensurate with the width of the sampling compounds 14 to be deposited on the filament 10.

In this method, a filament 10 is positioned with a location 16 centered between the walls 74 by sliding the filament 10 through flexible seals 76. The desired bath 46 of constituent material 50 is then pumped into the volume 71 to bond at the exposed location 16 of the filament, either directly to the filament 10 or to a previously bonded material of the sampling compounds 14. The bath 46 is then withdrawn from the volume 71 and the filament 10 repositioned. Then the same or different bath 46 may be introduced into the volume 71. In this case, no photo activation is necessary and the walls 74 act as an effective mask yet without the normal drawbacks of a masking process of changing the mask between different baths 46. A series of volumes 71 each separately filled with different or the same baths may be used to simultaneously treat a number of locations 16 long the filament 10.

Figure 14:
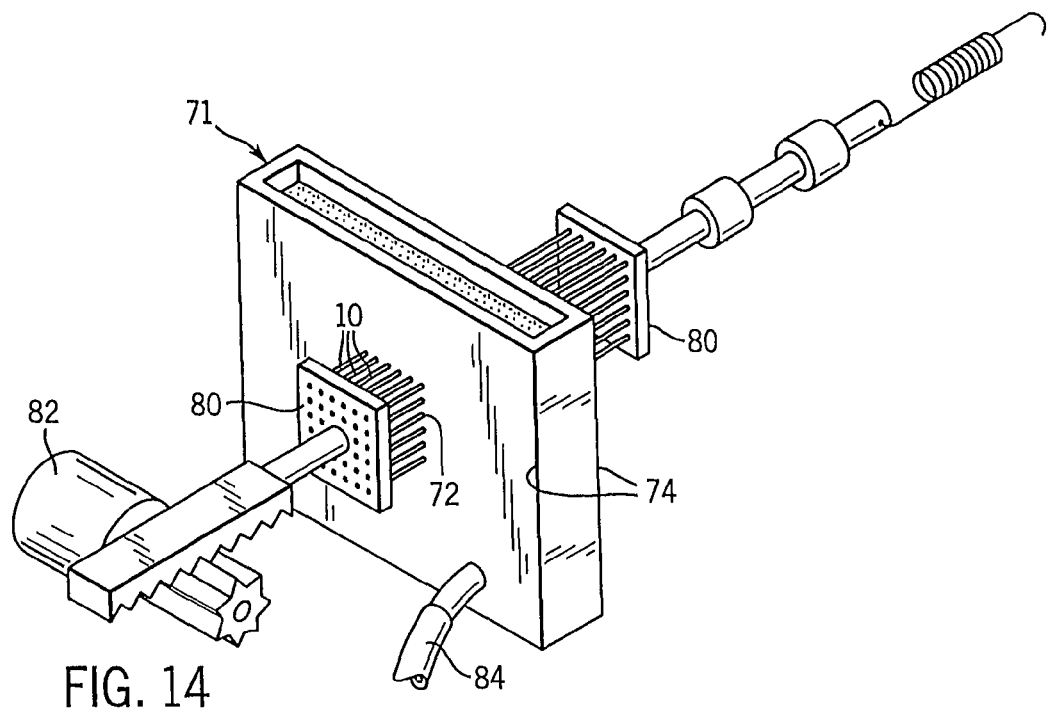
FIG. 14 is a perspective view of a manufacturing system employing the chambers of FIG. 13 for batch processing of a number of strips moved back and forth across the chamber.

Referring now to FIG. 14, this approach is also adaptable to the parallel processing of many filaments 10, the ends of which may be held by filament retention plates 80 positioned on either side of the walls 74 outside of the volume 71. The filament retention plates 80 hold the filaments in parallel fashion spaced from each other by an arbitrary distance along two axes perpendicular to the extent of the filaments 10. A positioning mechanism 82, preferably under computer control (similar to the controller 70 described with respect to FIG. 11) may reposition the filaments 10 within the volume 71 as different baths are introduced and withdrawn (also preferably under computer control) through an attached pipe 84.

Figure 15:
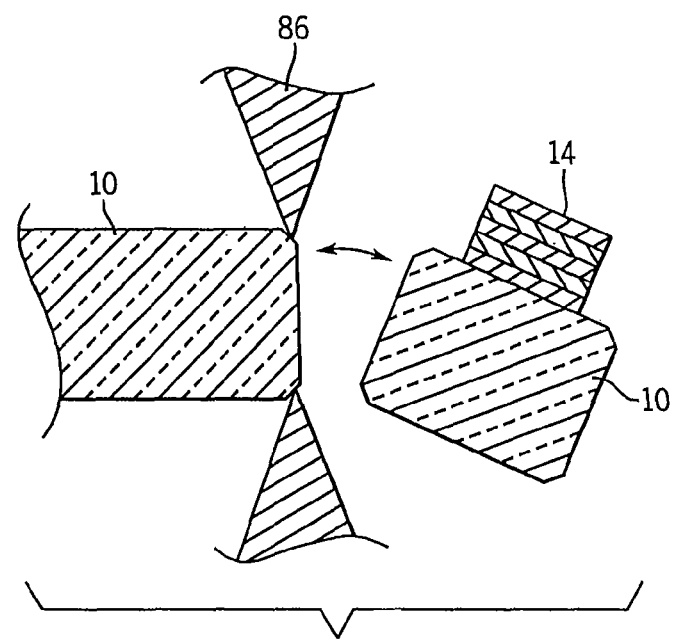
FIG. 15 is a cross-sectional view of a strip of the present invention showing breaking of the strip into bead-sized portions, each holding a single chemically reactive material.

Referring now to FIG. 15, although the present invention contemplates that the filaments 10 may be used as filaments, after the deposition of the necessary sampling compounds 14, the ability to easily process the filaments 10 also makes them attractive as a precursor to the production of beads. In this case, after deposition of the sampling compounds 14, the filament 10 may be sheared by cutter blades 86 into short segments at places between the locations 16, thus dividing the sampling compounds 14 from each other. In this way, the handling of separate beads during the deposition of the sampling compounds is eliminated. Further, because each of the sampling compounds 14 will be the same along a filament 10, the need for masks or tightly focused light beams is reduced or eliminated.

Figure 16:
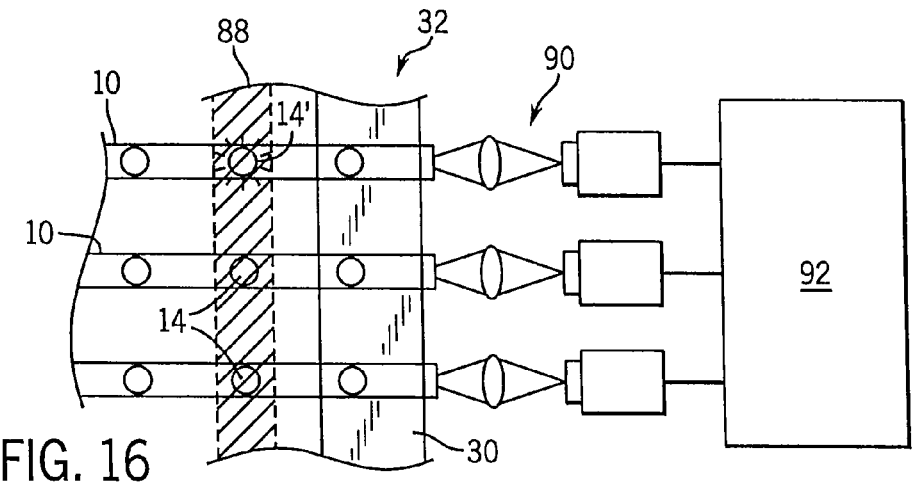
FIG. 16 is a schematic view of a plurality of strips formed of light conducting fibers and held in the frame of FIG. 3 coupled to photo detectors for detecting phosphorescence caused by a scanning columnar excitation illumination across the strips.

Referring now to FIG. 16, although one function of the filaments is to provide a flexible yet easy to handle substrate for the deposition of sampling compounds 14, by their nature, the filaments 10 also enable a number of novel reaction detection and reaction control techniques.

Referring now to FIG. 16, an array 32 of filaments assembled on a frame 30 may be used to test or assay a substance having a fluorescent marker. An excitation light source 88 may then be scanned across the rows described by the filaments 10 as held in the frame 30 causing fluorescence of given sampling compounds 14' where a reaction with the substance to be tested has occurred, and no fluorescence of other sampling compounds 14 that have not participated in such a reaction. If the filaments 10 are constructed of optical fibers, this fluorescence may be conducted to the ends of the filaments to be received by a light receptor 90 affiliated with each of the filaments 10. The light receptors may be photodiodes or phototransistors or other light detection devices well known in the art. A controller 92 coordinating the scanning of the excitation light source 88 and the detection of light from the given filaments may automatically identify those sampling compounds 14' at which hybridization has occurred by matching the position of the scanning light source 88 and the particular light receptor 90 providing a signal output.

Figure 17:
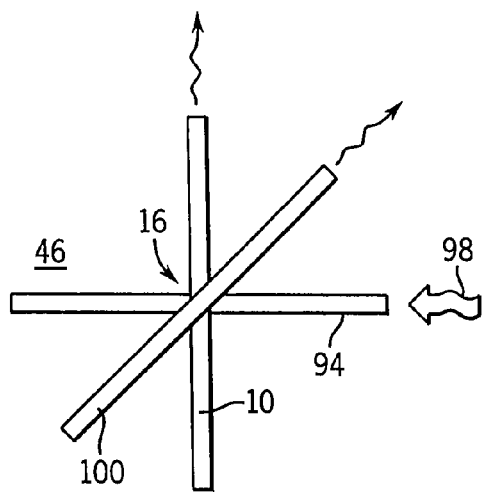
FIG. 17 is a simplified perspective view of orthogonally positioned strips also formed of light fibers and suitable for detecting localized phosphorescence without the need for an external scanning light source and suitable for use in multiple dimensions.

Referring to FIG. 17, the scanning excitation light source 88 may be replaced by an array of separate parallel optical fiber 94 crossing the given optical fiber filaments 10 at the locations 16 to conduct the excitation light 98 through themselves to the location 16 to produce fluorescence at the given sampling compound 14' on the filament 10 as shown in FIG. 16. Light lost through interstices between crossing filaments may serve to distinguish the location 16 from other locations through which the fluorescence may be conducted along more circuitous paths.

The introduction of yet another array of separate parallel optical fibers 100 orthogonal to both fibers 94 and filaments 10 allows this process to be extended into the three-dimensional array of FIG. 17 where the excitation light 98 is introduced into ones of fibers 94 and the florescence detected in pairs of the fibers 100 and filaments 10.

Alternatively, the two-dimensional configuration of FIG. 17 with crossing of only the fibers 94 and filaments 10 or the three dimensional crossing of fibers 94, 10 and 100 may be used to selectively encourage photo sensitive reactions at particular sampling compounds 14 through the introduction of light through two fibers 100 and 94 whose additive combination at the location 16 of particular sampling compound 14 within a bath 46 produce a threshold energy level sufficient for the reaction. In this way, fibers 94 and 100 and filaments 10 may conduct energy to control or initiate given reactions that may be of interest.

Each of the fibers 94 and 100 and filaments may have portions of the sampling compounds and their intersection may create the necessary juxtaposition of materials needed for a particular assay. In this way, a fixed library of filaments may be used to create a much greater variety of arrays 32 than would be dictated by a simple mathematical combination of the filament types.

Figure 18:
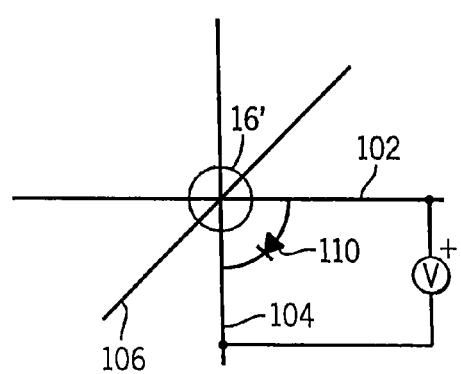
FIG. 18 is a schematic representation of a system similar to that of FIG. 17.

Referring now to FIG. 18, use of an electrically conducting strip for the substrate of a filament 10, allows electrical signals to be passed along orthogonal filaments 102, 104, and 106 crossing at location 16' to electrically or thermally activate chemical reactions or to electrically detect the results of those reaction through impedance or voltage measurements. So called, sneak electrical paths taking a more circuitous route through intersections of filaments 102, 106, and 104 and their neighbors may be eliminated by the deposition of a rectification material using semiconductor compounds on the outer surface of the fibers such as creates diodes 110 providing for a unique single conductive path from filament 102 to filament 104 through a single location 16'.

Example I

As one use of this invention, one may wish to screen expression patterns developed by a particular cell-type, under a given set of environmental stresses. Standard methods can be used for the extraction of RNA molecules from cells, followed by fluorochrome labeling. Many labeling schemes exist in the literature, which utilize direct incorporation during complementary strand synthesis, or covalent attachment with psoaralated compounds (see e.g. Lockhart, D. J. and Winzeler, E. A., "Genomic, gene expression and DNA arrays", *Nature*, 405, 827 (2000)). The resulting probes can be hybridized against a known array as described above with respect to FIG. 4 as one would for a conventional planar array.

Example II

Another possible utility of this invention is to screen multiple loci in a genome for rearrangements, insertions, and deletions. One prepares a number of PCR products using primer which will amplify across a known breakpoint. As an example, Prader-Willi syndrome (PWS) is most often caused by interstitial deletion of the chromosome segment 15q11-q13 from the paternally derived copy of chromosome 15. Similarly, Angelman syndrome (AS) involves a comparable maternal deletion. Thus, a series of PCR products could be prepare across the chromosomal segment 15q11-q13, using standard PCR techniques amplification protocols. Oligonucleotides can be synthesized using the present invention to screen or narrow down the breakpoint site. Since the region of this deletion is quite large, many thousands of oligonucleotides would have to be synthesized to cover the many possible breakpoint regions. Hybridization of fluorochrome-labeled PCR products against the synthesized oligonucleotides, would use standard protocols and procedures. These protocols are fully described on the website (microarrays.org/protocols.html), maintained by Prof. J. Derisi's laboratory (University of California, San Francisco). Another site maintained by TeleChem Corp, also list many useful protocols for mutation detection and fluorochrome-labeling: of probes: arrayit.com/DNA-Microarray-Protocols/#Protocol10.

Example III

Using the patterning technology described by the present invention, cells can be attached onto glass fibers. Simple incubation of treated fibers in cell culture will permit efficient attachment. Non-specific attachment of cells to glass surface can be made using standard protocols. For example, following the protocols of Webb, Hlady and Tresco (Webb K, Hlady V, Tresco P A. "Relative importance of surface wettability and charged functional groups on NIH 3T3 fibroblast attachment, spreading, and cytoskeletal organization.", J Biomed Mater Res. 1998 Sep. 5; 41(3):422-30), clean glass fibers (30% hydrogen peroxide in concentrated sulfuric acid, 30 minutes; followed by extensive washing with high purity water) can be treated with 1% 3-aminopropyltriethoxysilane (1% v/v in dry toluene), followed by further reaction with methyl iodide (5% v/v in redistilled absolute ethanol), to produce a quaternary amine. Prepared fibers can then be preincubated in fetal calf serum (5% in phosphate-buffer saline—PBS), and then incubated in harvested NIH 3T3 cells. Simple rinsing of fibers with PBS will remove unattached cells. Fibers holding attached cells can be stored for hours in PBS—for extended periods in cell culture media, housed in a cell culture incubator. The latter conditions would promote cell proliferation. A series of different cell type can be attached to different fibers and then assembled into mixed-cell arrays using the frame technology described in this invention. Arrays incubated under a broad range of conditions, followed by assays would permit simultaneous screening of a broad range of cell-type. Fluorogenic assays could be accomplished by incubating cells with labeled substrates, followed by imaging by fluorescence microscopy.

Cellular function is influenced by neighboring cells. Different cell-types, once arrayed as described above can be brought into designated proximity with each other by simple rearrangement cell-laden fibers. Crisscrossing of different cell-fiber arrays arranged in overlapping frames will allow a large number of different cell-cell interaction to be made—if a frame containing 100 different cell-types attached to 100 different fibers, then this would produce 10,000 combinations (this produces a matrix). The diagonal elements of this arrangement (thought of as a matrix) are the same cell-type arranged in proximity with itself, on two different fibers. This arrangement would serve as an excellent control. Intersections of cell types, on either side would also be redundant, with the cell-type pair existing on different fibers (matrix analogy: row and column). Again such redundancy would serve as excellent controls, or they could be eliminated by using a series of shortened fibers. Likewise a three-dimensional array of cell-types could be constructed by inter-crossing of cell-laden fibers in the x-, y- and z-dimensions.

It is specifically intended that the present invention not be limited to the embodiments and illustrations contained herein, but that modified forms of those embodiments including portions of the embodiments and combinations of elements of different embodiments also be included as comes within the scope of the following claims.

I claim:

1. A method of manufacturing strips of a non-reactive substrate extending along a longitudinal axis and supporting a linear array of different, chemically reactive substances exposed on a surface of the strip, the chemically reactive substances being spaced at locations along the longitudinal axis, the method comprising the steps of:
    (a) positioning a strip to simultaneously have different longitudinal portions within different volumes, each volume holding different component solutions;
    (b) light-activating a bonding between a substance of at least one of the component solutions and a longitudinal portion of the strip in at least one of the volumes, at one or more locations;
    (c) repositioning the strip to move the longitudinal portions among the different volumes; and
    (d) repeating steps (b) and (c) with light activation of the bonding of different substances in the different volumes and repositioning of the strip to synthesize different chemically reactive substances at the locations.

2. The method of claim 1 wherein the chemically reactive substances are oligonucleotides.

3. The method of claim 2 wherein the different volumes include at least four volumes each holding a different nucleotide.

4. The method of claim 1 wherein multiple strips are simultaneously positioned within the volumes to have light activated bonding of substances.

5. The method of claim 1 wherein the volumes are separated by a multiple of a distance between the locations of the chemically reactive substances.

6. The method of claim 1 wherein the strip is formed in a continuous loop to circulate through the volumes.

7. The method of claim 1 wherein the strip is an optical fiber.

8. The method of claim 1 wherein the strip is a glass fiber.

9. The method of claim 1 wherein the strip includes isolating bands of chemically repellent coating between the locations.

10. The method of claim 1 wherein the repositioning of step (d) moves the strip in different directions with different repeating of steps (b) and (c).

11. The method of claim 1 wherein the strip is clamped at opposing ends.

12. The method of claim 1 further including the step of dividing the strip into longitudinally smaller strips holding multiple different chemically reactive substances.

13. The method of claim 12 wherein the longitudinally smaller strips contain different series of chemically reactive substances.

14. The method of claim 1 further including the step of dividing the strip into beads each holding a single chemically reactive compound.

15. The method of claim 1 further including the step of marking the strips with a bar code.

16. The method of claim 1 including multiple strips and wherein the light-activating uses light sources focused into columnar form to cross the multiple strips.

* * * * *